(12) United States Patent  (10) Patent No.: US 9,095,281 B2
Sharma et al.  (45) Date of Patent: Aug. 4, 2015

(54) SEGMENTATION AND ENHANCED VISUALIZATION TECHNIQUES FOR FULL-RANGE FOURIER DOMAIN OPTICAL COHERENCE TOMOGRAPHY (71) Applicant: Carl Zeiss Meditec, Inc., Dublin, CA (US)

(72) Inventors: Utkarsh Sharma, San Leandro, CA (US); Homayoun Bagherinia, Oakland, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 359 days.

(21) Appl. No.: 13/761,404

(22) Filed: Feb. 7, 2013

(65) Prior Publication Data
US 2013/0208240 A1 Aug. 15, 2013

Related U.S. Application Data (60) Provisional application No. 61/597,579, filed on Feb. 10, 2012.

(51) Int. Cl.
*A61B 3/14* (2006.01)
*A61B 3/00* (2006.01)
(Continued)

(52) U.S. Cl.
CPC ............ *A61B 3/102* (2013.01); *G01B 9/02091* (2013.01); *G06T 7/0081* (2013.01); *G06T 7/0083* (2013.01); *G06T 2207/10101* (2013.01); *G06T 2207/30041* (2013.01)

(58) Field of Classification Search
CPC .......... A61B 3/103; A61B 3/14; A61B 3/113; A61B 3/1225; A61B 3/1015
USPC ................ 351/206, 221, 200, 205, 210, 246
See application file for complete search history.

(56) References Cited

U.S. PATENT DOCUMENTS 7,710,577 B2  5/2010  Yatagai et al.
8,363,225 B2  1/2013  Rolland et al.
(Continued)

FOREIGN PATENT DOCUMENTS

WO   2010/138645 A2   12/2010

OTHER PUBLICATIONS

International Search Report and Written Opinion received for PCT Patent Application No. PCT/EP2013/052543 mailed on May 15, 2013, 12 pages.
(Continued)

*Primary Examiner* — Dawayne A Pinkney
(74) *Attorney, Agent, or Firm* — Morrison & Foerster LLP (57) ABSTRACT

Presented here are new processing techniques for optical coherence tomography (OCT) data that allow for improved visualization and use of full-range OCT images. These techniques minimize the central line artifact and the complex conjugate artifact without requiring additional system hardware or significantly increasing post-processing time. The central line artifact is minimized by normalizing each A-scan to account for ripples at the zero-delay position. The complex conjugate artifact is minimized by segmentation of a layer or layers that cross the zero-delay position, and in some embodiments by further segmentation of other surfaces based on the segmentation of the initial layer or layers. The segmentation information is then used to selectively attenuate the complex conjugate image. It may also be used for other purposes, such as dewarping.

20 Claims, 9 Drawing Sheets

(51) Int. Cl.
  A61B 3/10    (2006.01)
  G01B 9/02    (2006.01)
  G06T 7/00    (2006.01)

(56) References Cited

U.S. PATENT DOCUMENTS

| 8,414,564 | B2 | 4/2013 | Goldshleger et al. | |
|---|---|---|---|---|
| 2009/0268159 | A1 | 10/2009 | Xu et al. | |
| 2012/0026462 | A1* | 2/2012 | Uhlhorn et al. | 351/206 |

OTHER PUBLICATIONS

Baumann et al., "Segmentation and Quantification of Retinal Lesions in Age-Related Macular Degeneration Using Polarizationsensitive Optical Coherence Tomography", Journal of Biomedical Optics, vol. 15, No. 6, Nov.-Dec. 2010, 9 pages.
Bonin et al., "In Vivo Fourier-Domain Full-Field OCT of the Human Retina With 1.5 Million A-lines/s", Optics Letters, vol. 35, No. 20, Oct. 15, 2010, pp. 3432-3434.
Costa R. A. et al., "Retinal Assessment Using Optical Coherence Tomography", Progress in Retinal and Eye Research, vol. 25, 2006, pp. 325-353.
Zhang et al., "Real-Time Dual-Mode Standard/Complex Fourier-Domain OCT System Using Graphics Processing Unit Accelerated 4D Signal Processing and Visualization", Proceeding of SPIE, vol. 7904, 2011, 7 pages.
Bachmann et al., "Heterodyne Fourier Domain Optical Coherence Tomography for Full Range Probing with High Axial Resolution", Optics Express, vol. 14, No. 4, Feb. 20, 2006, pp. 1487-1496.
Canny, John, "A Computational Approach to Edge Detection", IEEE Transactions on Pattern Analysis and Machine Intelligence, vol. PAMI-8, No. 6, Nov. 1986, pp. 679-698.
Choma et al., "Instantaneous Quadrature Low-Coherence Interferometry with 3 X 3 Fiber-Optic Couplers", Optics Letters, vol. 28, No. 22, Nov. 15, 2003, pp. 2162-2164.
Choma et al., "Sensitivity Advantage of Swept Source and Fourier Domain Optical Coherence Tomography", Optics Express, vol. 11, No. 18, Sep. 8, 2003, pp. 2183-2189.
Davis et al., "Heterodyne Swept-Source Optical Coherence Tomography for Complete Complex Conjugate Ambiguity Removal", Journal of Biomedical Optics, vol. 10, No. 6, Nov./Dec. 2005, pp. 064005-1-064005-6.
de Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.
Fischler et al., "Random Sample Consensus: A Paradigm for Model Fitting with Applications to Image Analysis and Automated Cartography", Communications of the ACM, vol. 24, No. 6, Jun. 1981, pp. 381-395.
Götzinger et al., "High Speed Full Range Complex Spectral Domain Optical Coherence Tomography", Optics Express, vol. 13, No. 2, Jan. 24, 2005, pp. 583-594.
Hofer et al., "Dispersion Encoded Full Range Frequency Domain Optical Coherence Tomography", Optics Express, vol. 17, No. 1, Jan. 5, 2009, pp. 7-24.
Hofer et al., "Fast Dispersion Encoded Full Range Optical Coherence Tomography for Retinal Imaging at 800 nm and 1060 nm", Optics Express, vol. 18, No. 5, Mar. 1, 2010, pp. 4898-4919.
Leitgeb et al., "Complex Ambiguity-Free Fourier Domain Optical Coherence Tomography through Transverse Scanning", Optics Letters, vol. 32, No. 23, Dec. 1, 2007, pp. 3453-3455.
Leitgeb et al., "Performance of Fourier Domain vs. Time Domain Optical Coherence Tomography", Optics Express vol. 11, No. 8, Apr. 21, 2003, pp. 889-894.
Leitgeb et al., "Phase-Shifting Algorithm to Achieve High-Speed Long-Depth-Range Probing by Frequency-Domain Optical Coherence Tomography", Optics Letters, vol. 28, No. 22, Nov. 15, 2003, pp. 2201-2203.
Leitgeb et al., "Ultrahigh Resolution Fourier Domain Optical Coherence Tomography", Optics Express, vol. 12, No. 10, May 17, 2004, pp. 2156-2165.
Sarunic et al., "Instantaneous Complex Conjugate Resolved Spectral Domain and Swept-Source OCT using 3×3 Fiber Couplers", Optics Express, vol. 13, No. 3, Feb. 7, 2005, pp. 957-967.
Timp et al., "A New 2D Segmentation Method Based on Dynamic Programming Applied to Computer Aided Detection in Mammography", Medical Physics, vol. 31, No. 5, May 2004, pp. 958-971.
Tomasi et al., "Bilateral Filtering for Gray and Color Images", Proceedings of the 1998 IEEE International Conference on Computer Vision, Bombay, India, 1998, 8 pages.
Vakoc et al., "Elimination of Depth Degeneracy in Optical Frequency-Domain Imaging through Polarization-Based Optical Demodulation", Optics Letters, vol. 31, No. 3, Feb. 1, 2006, pp. 362-364.
Wang, Ruikang K., "In Vivo Full Range Complex Fourier Domain Optical Coherence Tomography", Applied Physics Letters, vol. 90, 2007, pp. 054103-1-051403-3.
Westphal et al., "Correction of Geometric and Refractive Image Distortions in Optical Coherence Tomography Applying Fermat's Principle", Optics Express, vol. 10, No. 9, May 6, 2002, pp. 397-404.
Wojtkowski et al., "Full Range Complex Spectral Optical Coherence Tomography Technique in Eye Imaging", Optics Letters, vol. 27, No. 16, Aug. 15, 2002, pp. 1415-1417.
Yasuno et al., "Simultaneous B-M-Mode Scanning Method for Real-Time Full-Range Fourier Domain Optical Coherence Tomography", Applied Optics, vol. 45, No. 8, Mar. 10, 2006, pp. 1861-1865.
Yun et al., "Motion Artifacts in Optical Coherence Tomography with Frequency-Domain Ranging", Optics Express, vol. 12, No. 13, Jun. 28, 2004, pp. 2977-2998.
Zhang et al., "Removal of a Mirror Image and Enhancement of the Signal-to-Noise Ratio in Fourier-Domain Optical Coherence Tomography Using an Electro-Optic Phase Modulator", Optics Letters, vol. 30, No. 2, Jan. 15, 2005, pp. 147-149.

* cited by examiner

SEGMENTATION AND ENHANCED VISUALIZATION TECHNIQUES FOR FULL-RANGE FOURIER DOMAIN OPTICAL COHERENCE TOMOGRAPHY

PRIORITY

This application claims priority to U.S. Provisional Application Ser. No. 61/597,579 filed Feb. 10, 2012 hereby incorporated by reference.

TECHNICAL FIELD OF THE INVENTION

The present invention relates to medical imaging, and in particular, data acquisition and processing methods for data acquired through optical coherence tomography (OCT).

BACKGROUND

Optical coherence tomography (OCT) is an optical imaging technology for performing in situ real-time cross-sectional imaging of tissue structures at a resolution of less than 10 microns. OCT measures the scattering profile of a sample along the OCT beam. Each scattering profile is called an axial scan, or A-scan. Cross-sectional images, called B-scans, and by extension 3D volumes, are built up from many A-scans, with the OCT beam moved to a set of transverse locations on the sample.

In recent years, it has been demonstrated that Fourier domain OCT (FD-OCT) has advantages over the original time-domain OCT (TD-OCT) (R. A. Leitgeb et al., "Performance of fourier domain vs. time domain optical coherence tomography," Optics Express 11(8): 889-94 (2003); J. F. de Boer et al., "Improved signal-to-noise ratio in spectral-domain compared with time-domain optical coherence tomography," Optics Letters 28(21): 2067-69 (2003); M. A. Choma et al., "Sensitivity advantage of swept source and Fourier domain optical coherence tomography," Optics Express 11(18): 2183-89 (2003)). In TD-OCT, the optical path length between the sample and reference arms needs to be mechanically scanned. In FD-OCT, on the other hand, the optical path length difference between the sample and reference arm is not mechanically scanned. Instead, a full A-scan is obtained in parallel for all points along the sample axial line within a short time, determined by the wavelength sweep rate of a swept source in swept-source OCT (SS-OCT) or the line scan rate of the line scan camera in spectral-domain OCT (SD-OCT). As a result, the speed for each axial scan can be substantially increased as compared to the mechanical scanning speed of TD-OCT.

The spectral interferogram acquired through FD-OCT encodes the longitudinal sample structure at the focal spot. To recover the sample structure, the interference pattern can be inverse Fourier transformed. The inverse Fourier transform yields three components: the DC component, cross-correlation component, and auto-correlation component. The DC terms are often the largest component and are pathlength-independent. The cross-correlation terms contain the information of interest—the sample reflectivity profile. The auto-correlation terms represent interference between the different reflectors within the sample. Elements of all three of these components can lead to artifacts that can cause problems in data interpretation or processing.

In OCT signal processing, DC terms are normally suppressed by performing a processing step known as background subtraction. However, due to temporal variations in the detected power levels, the DC terms are often not fully subtracted. One artifact, the central line artifact, results due to the residual DC terms. This artifact manifests as a bright central line that could be several pixels thick and is near the zero optical delay position. The bright line artifact due to the residual DC terms can overwhelm the overlapping information of interest in the cross-correlation component.

Another artifact is the complex conjugate artifact, which arises from the cross-correlation terms. The complex conjugate artifact is a mirror image of the true image that appears on the opposite side of the zero-delay position—the virtual position where the optical path length in the sample arm equals that of the reference arm. In some cases the mirror image is distorted due to dispersion mismatch in the two arms of the interferometer, causing it to appear blurred. The complex conjugate artifact can lead to ambiguity in image interpretation as well as erroneous analysis of the OCT data.

To avoid the effects of both the central line artifact and the complex conjugate artifact, the zero-delay position is often chosen so that it is located outside of the sample region. Both artifacts can then be removed by using only the positive or negative space. However, ensuring that the zero-delay position is not located within the sample effectively halves the available imaging depth. Data acquisition or processing methods that minimize the effect of the central line and complex conjugate artifacts without needing to keep the zero-delay position outside of the sample area, and therefore allowing double the OCT range, are thus highly desirable. The resulting ability to acquire extended-depth or full-range OCT can be extremely useful for biomedical imaging applications such as imaging of the anterior segment of the eye.

One of the standard methods for minimizing the DC contribution and hence the signal at and near the zero-delay is background subtraction. This can be done by subtracting the signal when no sample is present from the signal acquired with a sample. However, background subtraction alone may be insufficient for minimizing the DC artifact due to ripples in the reference light. Therefore, a method to better minimize the central line artifact is desirable.

Several full-range OCT imaging techniques capable of removing or minimizing the complex conjugate artifact have been demonstrated. Hardware-based approaches to solve this issue have included stepping phase-shifting in the reference arm using piezo-mounted reference mirrors, electro-optic modulators, carrier-frequency shifting methods, quadrature interferometers, and polarization diversity. Hardware-based approaches, however, add cost and complexity of the system, and several approaches have technical limitations. The phase-shifting methods are vulnerable to reduced performance due to inaccuracy in phase shifts (chromatic errors), sample motion, and mechanical instability of the interferometer. Electro-optic and acousto-optic (AO) modulator-based methods add costly components and add complexity for broadband operations. Quadrature interferometers using 3×3 couplers require an additional detection channel, careful calibration, and suffer from wavelength-dependent splitting ratio variations for broadband operations. Polarization diversity methods run into problems due to sample birefringence. There are also some techniques for full-range OCT that use continuously changing phase shifts between densely spaced A-scans. However, subject motion may result in imaging artifacts and reduced performance of complex conjugate suppression.

Other techniques rely on specialized algorithms to reduce or remove the complex conjugate artifact. The majority of these methods require multiple frame acquisitions and heavy post-processing, which make them slower for real-time display and visualization. Hofer et al. demonstrated a dispersion encoded full-range (DEFR) algorithm that uses the dispersion mismatch between sample and reference arm to iteratively suppress complex conjugate artifacts on an A-scan by A-scan basis (B. Hofer et al., "Dispersion encoded full range frequency domain optical coherence tomography," Opt. Express 17(1): 7-24 (2009) hereby incorporated by reference). While this technique may have favorable application in anterior segment imaging, the algorithm is time-consuming, and requires the sample and reference arm to have a large dispersion mismatch, thereby enforcing additional hardware design-related constraints on the interferometer module. In addition, all of the above mentioned techniques may reduce but not fully minimize the artifact. It would be desirable to have an OCT imaging technique capable of removing or minimizing the complex conjugate artifact without these drawbacks that could be used alone or in combination with other techniques.

The existence of the complex conjugate artifact may lead to failures in analysis algorithms such as tissue layer segmentation. Segmentation of anatomical structures in full-range anterior segment B-scans is crucial for the diagnosis and study of anterior segment diseases. Manual segmentation, however, is subjective and time consuming. It is therefore desirable to have a tissue segmentation algorithm that can be used with full-range OCT images containing complex conjugate artifacts or an otherwise cluttered background; this would be an important step towards faster and reliable quantification.

The ability to segment tissue layers in full-range OCT images with complex conjugate artifacts also enables the application of other algorithms that rely on segmentation, such as thickness analysis and dewarping. In OCT imaging, refraction at the interface of two mediums having different refractive indices can cause image distortions. Refraction-related distortions are especially problematic in anterior segment imaging due to the large difference in the refractive indices of air and corneal tissue (approximately 0.38). The distortions can be corrected using dewarping techniques (V. Westphal et al., "Correction of geometric and refractive distortions in optical coherence tomography applying Fermat's principle," Opt. Express 10(9): 397-404 (2002)), but correct segmentation of layer interfaces is essential to proper dewarping.

SUMMARY

Here, we propose several new OCT data processing techniques that allow improved visualization of extended-depth, refraction-corrected, full-range OCT images. These techniques minimize the central line artifact and the complex conjugate artifact without requiring additional hardware in the system or significantly increasing the post-processing time. Because this method does not require any changes in the OCT hardware, it is cost-effective and allows for easy upgrading of existing systems. The methods also do not require multiple acquisitions at the same location, which means that acquisition time is not increased.

In the invention described herein, we minimize the modulation ripples at the zero-delay position by normalizing each A-scan. We also display the full-range OCT image, differentiate and segment out the real image from the mirror image, provide an adjustable control to fade out the mirror image, minimize artifacts in full-field OCT images, and perform dewarping based on the segmentation results of the real and mirror images.

One of the key steps in our method for minimizing the complex conjugate artifact involves segmentation of a layer that spans the real and mirror images. In one embodiment of the invention, a segmentation algorithm is designed to identify the boundaries of the anterior and posterior corneal surfaces, as well as the iris and lens capsule surfaces in a 2D B-scan, where at least one of the surfaces extends onto both sides of the zero-delay position. The output of this segmentation can be used to attenuate the mirror image artifact. It can also be used for dewarping the full-range OCT image in order to represent the true anatomical information of the sample such as the anterior segment of the eye. Full-range anterior segment B-scans can provide an overall view of the anterior chamber and the configuration of bilateral irido-corneal angles in one glance.

DETAILED DESCRIPTION

Figure 1:
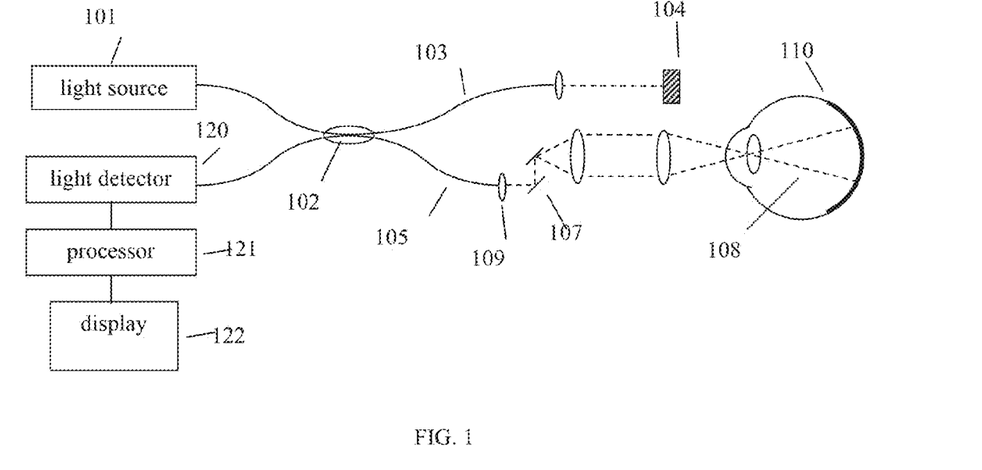
FIG. 1 is a diagram of a generalized frequency-domain OCT system for use in ophthalmology.

A diagram of a generalized frequency-domain OCT (FD-OCT) system for use in ophthalmology is shown in FIG. 1. Light from source 101 is routed, typically by optical fiber 105, to illuminate the sample 110, a typical sample being tissue in the human eye. Typical sources are a broadband light source with short temporal coherence length in the case of spectral-domain OCT (SD-OCT), or a wavelength-tunable laser source in the case of swept-source OCT (SS-OCT). The beam of light (dashed line 108) is scanned laterally (in x and y, if z is parallel to the beam of light) over the area or volume to be imaged, typically with scanning optics 107 between the output of the fiber and the sample. Light backreflected from the sample returns through scanning optics 107 and is collected, typically into the same fiber 105 used to route the light for sample illumination. Lens 109 is used to collimate the illuminating light exiting the fiber and to focus the reflected light back into the fiber for collection. Reference light derived from the same source 101 travels a separate path, in this case involving fiber 103 and retro-reflector 104 with an adjustable optical delay. Those skilled in the art will recognize that a transmissive reference path can also be used and that the adjustable delay could be placed in either the sample or reference arm of the interferometer. Additionally, the interferometer could consist of fiber optics, bulk optical components, or a combination thereof. Collected sample light is combined with reference light, typically in a fiber coupler 102, to form light interference in a detector 120. Although a single fiber port is shown going to the detector, those skilled in the art will recognize that various designs of interferometers can be used for balanced or unbalanced detection of the interference signal. The output from the detector is supplied to a processor 121. The results can be stored in the processor 121 or displayed on display 122. The processing and storing functions may be localized within the interferometric data collection instrument or functions may be performed on an external processing unit to which the collected data is transferred. This unit could be dedicated to data processing or perform other tasks which are quite general and not dedicated to the OCT imaging device.

The interference between the light returning from the sample and from the reference arm causes the intensity of the interfered light to vary across the spectrum. The Fourier transform of the interference light reveals the profile of scattering intensities at different path lengths, and therefore scattering as a function of depth (z-direction) in the sample (see for example R. Leitgeb et al., "Ultrahigh resolution Fourier domain optical coherence tomography," Opt. Express 12(10): 2156-65 (2004)). The scattering profile as a function of depth is called an axial scan (A-scan). A set of A-scans measured at neighboring locations in the sample produces a cross-sectional image (tomogram or B-scan) of the sample. A collection of B-scans makes up a data cube or volume. It should be noted, however, that the application of these methods need not be limited to data acquired via FD-OCT; they could also be applied to data acquired via other OCT variants including TD-OCT. The methods of the present invention can be applied to OCT data collected using systems designed to reduce the complex conjugate artifact to further reduce the impact of artifacts on the collected data.

Minimizing Central Line Artifact by Normalization of A-Scan Spectra in B-Scans

Figure 2:
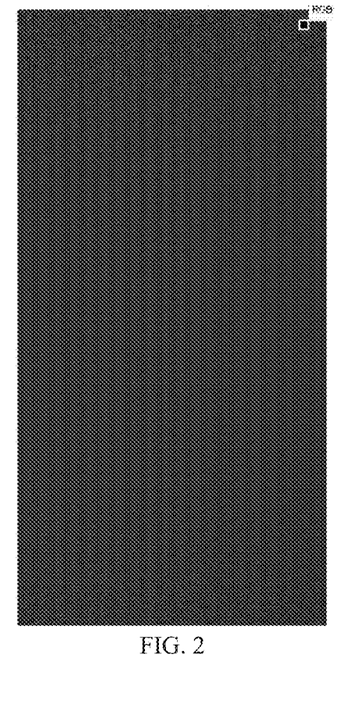
FIG. 2 is a reference spectral frame after background subtraction.

As described above, the DC component of the spectral interferogram acquired through FD-OCT can lead to a central line artifact near the zero-delay position. One of the standard methods for minimizing the DC contribution and hence the signal at and near the zero-delay is background subtraction. This can be done by subtracting the background reference signal from the signal acquired with a sample. In the preferred embodiment, background signal is obtained by averaging multiple spectral measurements of the reference light alone. However, background subtraction alone may be insufficient for minimizing the DC artifact. In images from an SD-OCT system, small modulations in the reference power collected by the spectrometer are apparent after the difference between the reference frame and average reference spectra (i.e. the background signal) is plotted. FIG. 2 shows a reference spectral frame (1024×2048) from a 2048-pixel camera with background signal subtracted. There, the background signal was calculated by averaging the measurements across the frame (i.e. averaging the 1024 spectral interferograms). Periodic ripples in intensity are clearly visible, with spacing of approximately 50-60 pixels. The source of these ripples may be due to fluctuations in the superluminescent diode (SLD) light output or the reference power, or may be the result of non-uniform integration times at the CCD camera.

Figure 3:
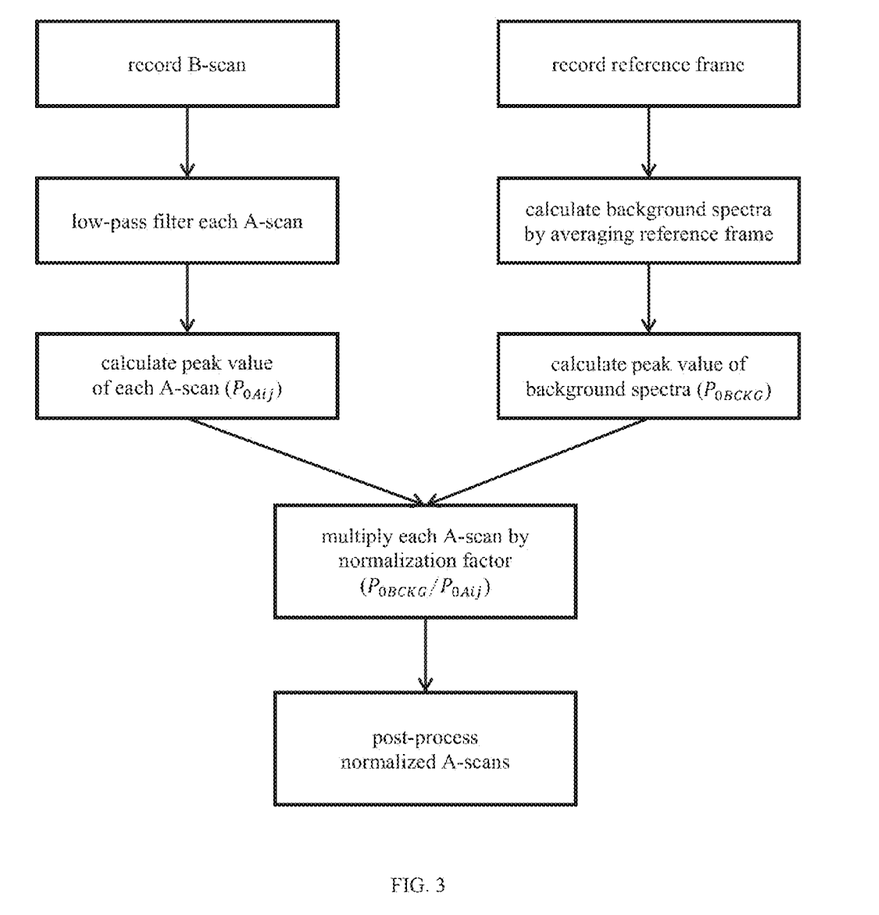
FIG. 3 illustrates an embodiment of an algorithm for normalizing the data and minimizing the central line artifact.

Here we propose a solution in which each spectral interferogram corresponding to an A-scan can be normalized to minimize the effect of modulations in reference power, leading to smaller DC residual terms and hence minimization of the central line artifact. FIG. 3 illustrates an embodiment of an algorithm for normalizing the data and minimizing the central line artifact. As illustrated in FIG. 3, first a B-scan of the sample and a reference frame (a B-scan without a sample present) are acquired. The background signal is then calculated by averaging together all of the A-scans in the reference frame. The peak value of the background signal, $P_{0BCKG}$, is then calculated. Each spectral measurement from the B-scan (or A-scan) is then low-pass filtered along the length of the A-scan. The peak value of each low-pass filtered A-scan, $P_{0Aij}$, is then calculated. Low-pass filtering removes fringe modulations due to interference and allows measurement of reference signal levels in each A-scan. Each A-scan is then multiplied by the normalization factor $P_{0BCKG}/P_{0Aij}$, such that $$A_{ij} = A_{ij}\left(\frac{P_{0BCKG}}{P_{0Aij}}\right).$$

Figure 4A:
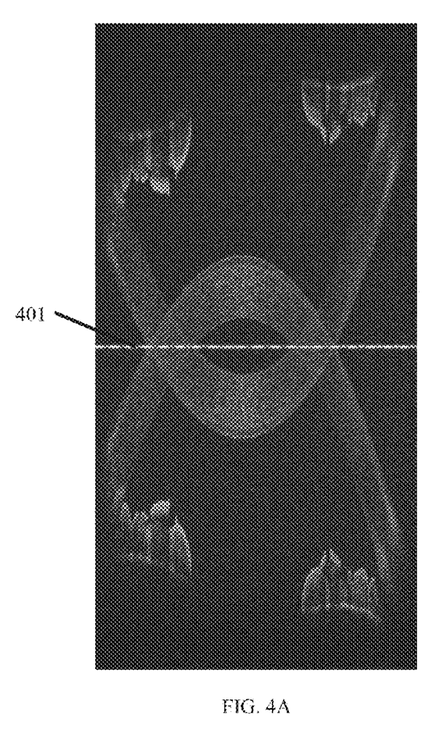
FIG. 4A is a full-range anterior segment B-scan before normalization correction.
Figure 4B:
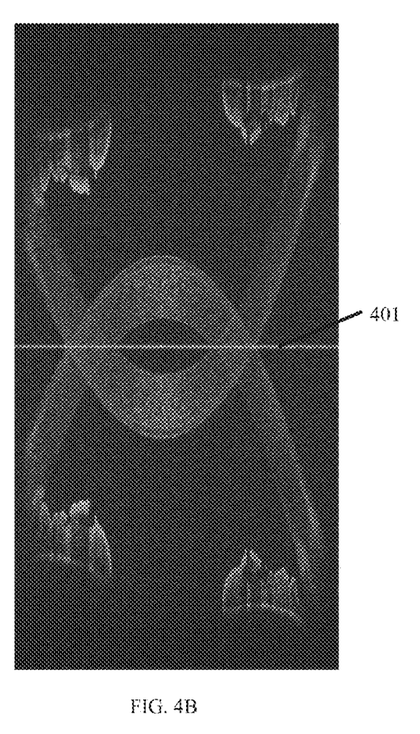
FIG. 4B is a full-range anterior segment B-scan after normalization correction.

Standard OCT post-processing steps, such as background signal subtraction, dispersion correction, and Fourier transformation, are then carried out using the normalized A-scan spectra. FIGS. 4A-B show the result of using this technique. FIG. 4A shows the full-range OCT image without normalization correction, and FIG. 4B shows the image after correction. The periodic strong central line artifact 401 is relatively suppressed in FIG. 4B as compared to FIG. 4A.

The preferred method described in the algorithm involves the use of a separate reference frame for calculation of the background signal. However, the invention can also be realized by calculating the background signal without acquiring a separate reference frame. Instead, multiple A-scans across several transverse locations in the B-scan can be averaged to obtain the background reference signal. Because the interference fringes change rapidly at different transverse locations, such averaging could approximate the DC reference component.

Minimization of the central line artifact is just one aspect of the present invention directed toward improving visualization of full-range OCT images. It can be combined with the segmentation aspect of the invention described in the following section, or used on any OCT B-scan that displays an artifact at zero-delay.

Figure 5:
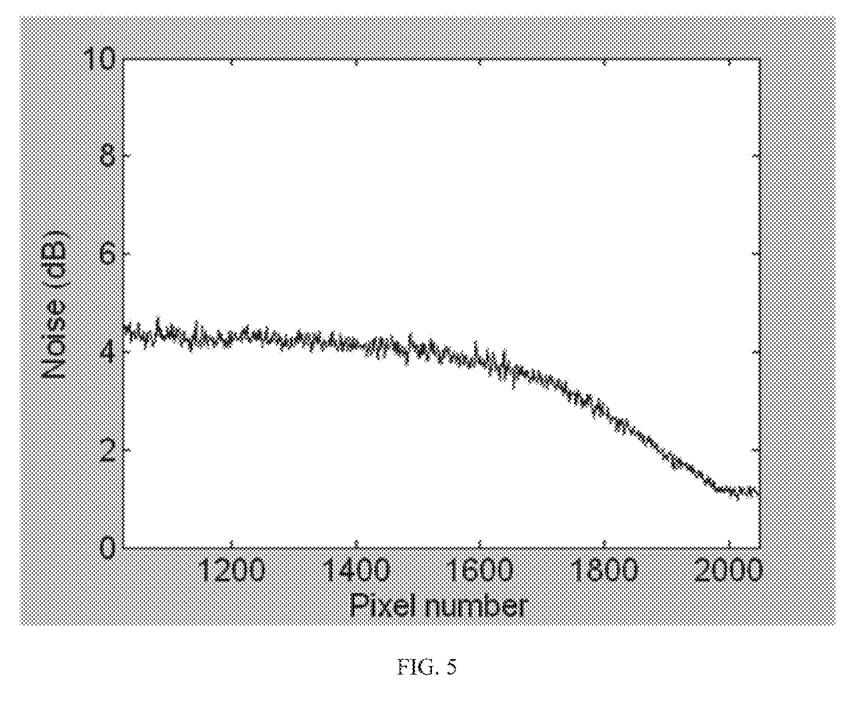
FIG. 5 shows the reconstructed background spectrum/noise floor.

Visualization of the OCT data can also be enhanced by flattening the noise floor across each A-scan. After each A-scan is reconstructed from the raw data collected by the OCT system, the noise floor may not be completely flat. That is, if all of the A-scans of a B-scan containing only noise are averaged along each depth location, the average noise value may vary with depth location. FIG. 5 shows the average of all A-scans from a noise-only B-scan as a function of depth, with only the lower half of the full-range data shown (pixels 1024 to 2048 of a full-range B-scan with A-scans 2048 pixels long). One can observe that the noise floor is uneven and decreases at higher pixel values. This causes uneven brightness levels across the depth positions of a reconstructed A-scan.

This unevenness can be compensated for by adjusting the brightness at each depth position. The brightness adjustment can be done using an adjustment offset vector having the same dimensions as the A-scan. The adjustment offset vector can be computed by first reconstructing the raw background A-scans. The reconstructed background A-scans are then averaged to produce a single averaged A-scan. The average A-scan is then smoothed with a median filter. The maximum value of the smoothed vector is then computed, excluding the center part of the vector due to the strong signal at zero-delay, which is always located around the center of each A-scan.

Finally, the adjustment offset for each position is computed by subtracting the smoothed vector from its maximum value. The adjustment offset vector is added to each new reconstructed A-scan to produce an A-scan with flattened noise floor.

Robust Automatic Segmentation of Full-Range FD-OCT Images for Artifact Reduction The method described here is able to segment layers in full-range OCT images containing a variety of artifacts or imaging deficiencies including but not limited to: complex conjugate artifacts, cluttered background, low SNR around the layers, changing iris shape due to pupil dilation, and other different artifact types. In particular, the method described here involves segmenting layers in full-range OCT images in which at least one tissue surface extends to both sides of the zero-delay position. Placing the sample across the zero-delay position allows the full imaging depth to be used, but, as described above, makes segmentation and removal of the complex conjugate difficult because the true image and the complex conjugate image will have regions of overlap. If instead the sample is kept entirely on one side of the zero-delay position, then the complex conjugate image will fall entirely on other side of the zero-delay position, and overlap of the real and complex conjugate images will then be avoided. However, in doing so, the usable imaging depth is limited to only half of the full-range OCT imaging depth. This is undesirable for several OCT imaging applications requiring greater depth, such as imaging of the anterior segment of the eye. In the invention described here, the ability to segment full-range OCT images in which the true image and complex conjugate overlap allows for attenuation of the complex conjugate, as well as enabling quantitative morphological analysis of the wide field OCT images of the anterior segment with the help of measurements tools such as calipers. These quantitative morphological analyses include irido-corneal angle measurement, angle-to-angle measurement, central corneal thickness, and anterior chamber depth measurement. The segmented layers can also be used for dewarping and for the flap tool that measures the flap and stromal thickness at any position. In addition, however, the technique described below can also work with OCT images without complex conjugates or cluttered backgrounds.

The segmentation approach takes advantage of several pieces of prior knowledge: that the general shape of a cornea is a quadric surface; that the general shape of a meridian is a quadratic function; the approximate lateral and axial positions of the vertex; the approximate corneal thickness; and the approximate anterior and posterior surface curvatures. The steps of the segmentation and mirror image removal algorithm can be summarized as follows: (1) preprocessing; (2) anterior and posterior layer segmentation; (3) iris surface and lens capsule segmentation; and (4) mirror image attenuation. The segmentation information can also be used for other purposes, such as refraction correction and dewarping. While the embodiment of the algorithm described here is as applied to imaging of the anterior segment of the eye, the algorithm could also be applied to imaging of other surfaces, such as the retina.

In the preferred embodiment, the preprocessing step comprises bilateral filtering (see C. Tomasi and R. Manduchi, "Bilateral filtering for gray and color images," Proc. ICCV: 839-46 (1998)). The bilateral filter is an edge-preserving and noise-reducing smoothing filter. The intensity value at each pixel in an image is replaced by a weighted average (based on a Gaussian distribution) of intensity values from nearby pixels, where the weights depend not only on spatial position but also on the differences in the intensity range. This filtering method makes the performance of the following segmentation step more robust. Other preprocessing steps could be envisioned by one skilled in the art.

The anterior and posterior layers of the cornea are then segmented. To accomplish this in the preferred embodiment of the present invention, Canny edge detection is first implemented, resulting in a binary image where a pixel having a "1" value represents an edge (see J. Canny, "A computational approach to edge detection," IEEE Transactions on Pattern Analysis and Machine Intelligence PAMI-8(6): 679-98 (1986), hereby incorporated by reference). A region of interest (ROI) is then extracted from the Canny image, where the ROI is defined as the upper half of the original image. This ROI contains the central portion of the anterior and posterior corneal surfaces. Within the ROI, the connected edges are identified, where a connected edge is defined as multiple adjacent pixels having a "1" value. (Two pixels are defined as adjacent if one is located in one of the eight pixels surrounding the other.)

Quadratic functions are then robustly fitted to identified connected edges having a threshold number of connected pixels, where the threshold value is determined based on the image size. Thus, the number of quadratic functions that are fitted depends on the number of connected edges found in the ROI that meet this threshold. This number may be significantly more than the anatomical edges found in the sample because many of the "edges" identified by Canny edge detection may be due to noise, and others may be due to the complex conjugate. In a preferred embodiment, the quadratic function is a parabola ($y=ax^2+bx+c$). The quadratic function's parameters can be determined using Random Sample Consensus (RANSAC) fitting (see M. A. Fischler and R. C. Bolles, "Random Sample Consensus: A paradigm for model fitting with applications to image analysis and automated cartography," Comm. of the ACM 24(6): 381-95 (1981), hereby incorporated by reference). RANSAC assumes that the data contains points that are gross errors or outliers, in addition to other data points that are inliers and whose distribution can be explained by some set of model parameters. As such, it is a more robust fitting method and is able to smooth data sets in which outliers make up a significant portion of the data set.

From the quadratic functions fitted to the connected edges, two are identified as corresponding to the anterior and posterior corneal layers and used for the initial estimates of the layer positions. These two quadratic functions are selected based on a number of known characteristics: First, since the anterior and posterior surfaces of the cornea are approximately parallel to each other, the two quadratic functions fitted to them are assumed to be approximately parallel to each other. Second, the quadratic functions are assumed to have a distance between them within the range of corneal thickness. Third, the two quadratic functions are assumed to have similar curvature with a concave shape, with that curvature falling within the range of corneal anterior and posterior curvatures. Fourth, their vertices are assumed to have similar x-coordinates and to be located in the central part of the image laterally. The upper quadratic function serves as the initial estimate of the anterior corneal surface, and the lower quadratic function serves as the initial estimate of the posterior corneal surface.

After the initial estimates are identified, final layer positions can be determined using hybrid graph theory and dynamic programming framework (see S. Timp, "A new 2D segmentation method based on dynamic programming applied to computer aided detection in mammography," Med. Phys. 31(5): 958-71 (2004), hereby incorporated by reference). In one embodiment of the method, the regions around the quadratic function fits to the anterior and posterior layer positions are used to define ROIs. In another embodiment of the method, only one parabola is selected—either the initial estimate of the anterior surface or the initial estimate of the posterior surface—and the ROI is defined based on the single parabola and prior knowledge about average corneal thickness. In yet another embodiment of the method, the average of the lower and upper parabolas is used to define an ROI, again taking advantage of the prior knowledge about average corneal thickness.

Graph-based segmentation can then be performed within the ROIs. The graph-based method segments the corneal layers in a piecewise manner, segmenting the central regions of the layers (those falling above the zero-delay position) and the left and right regions of the layers (falling below the zero-delay position). The regions of the layers falling at the zero-delay position are extrapolated from the three segmented regions. The central, left, right, and extrapolated regions are then combined to create the full, continuous layer segmentations.

Figure 6:
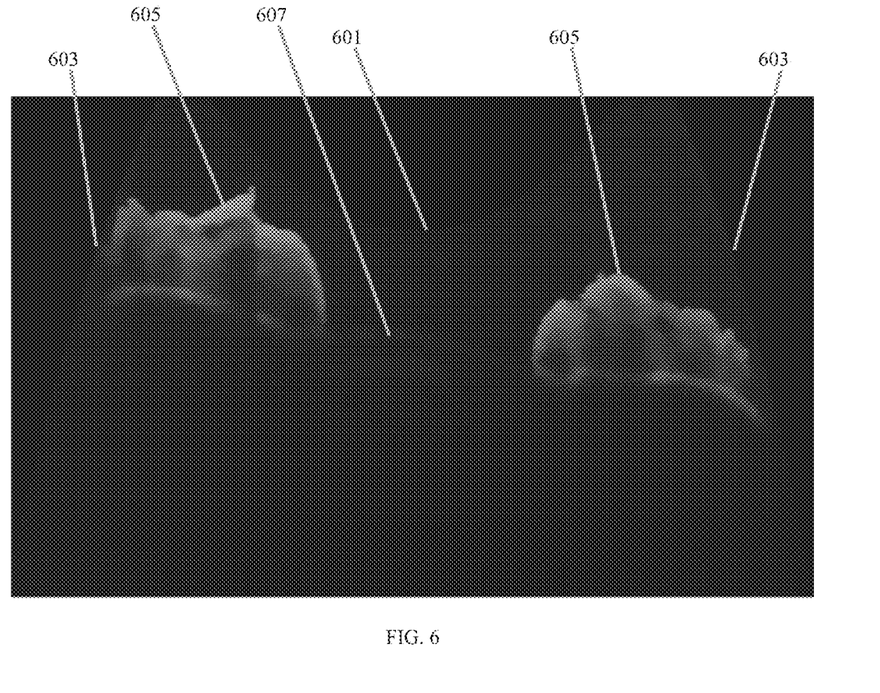
FIG. 6 shows a region of interest (ROI) for segmentation of the iris and anterior surface of the lens capsule.

After the final positions are determined for the anterior and posterior layers of the cornea, their positions can be used to aid further segmentation of areas of interest in the image. For example, the final positions can be used to aid segmentation of the iris and anterior surface of the lens capsule. As shown in FIG. 6, the ROI containing the iris 605 and anterior surface of the lens capsule 607 can be defined as the area in the lower half of the full image that is (1) below the mirror image (across the zero-delay position) of the anterior corneal surface 601 and (2) below the posterior corneal surface 603. Graph-based segmentation is can then be used to estimate the iris and lens surface positions. The posterior surface of the lens can also be segmented using the knowledge of the anterior surface of the lens to define an ROI within which graph-based segmentation is performed. From the anterior and posterior surfaces of the lens, the lens thickness can be calculated based on the distances between the anterior and posterior surfaces.

Figure 7A:
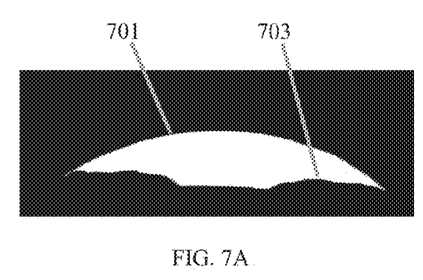
FIG. 7A shows a mask generated from the posterior corneal surface and iris/lens surfaces.
Figure 7B:
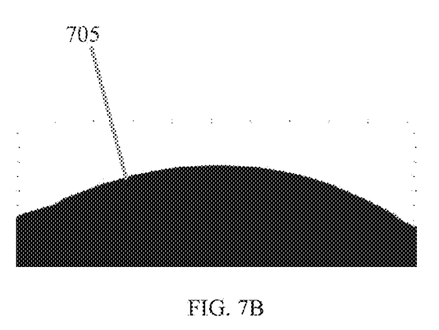
FIG. 7B shows a mask generated from the anterior corneal surface.
Figure 8A:
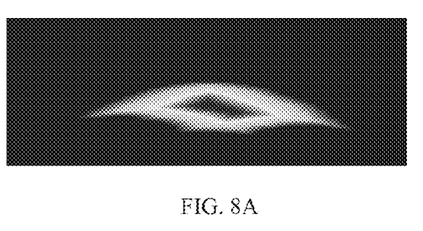
FIGS. 8A-B show distance transforms of the masks in FIGS. 7A-B.
Figure 8B:
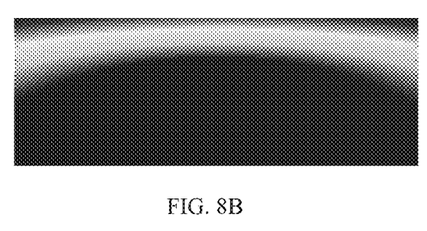

Once the necessary layers are segmented, the mirror image can then be attenuated. In the preferred embodiment of the invention, the mirror image attenuation is performed by generating two masks based on the segmented anterior and posterior corneal surfaces and the iris/lens surfaces. The masks are generated from two images with the same dimensions as a B-scan, having all pixel values initially set to 0. Then, as shown in FIG. 7A, to create the first mask, all of the pixel values between the posterior corneal surface 701 and the lens/iris surface 703 are set to the value "1". The black in FIG. 7A indicates pixel values set to "0", and white indicates pixel values set to "1", To create the second mask, shown in FIG. 7B, all of the pixel values above the anterior corneal surface 705 are set to "1", A distance transform is then used to smooth the transition at the mask edges, as shown in FIGS. 8A-B. FIG. 8A shows the mask from FIG. 7A with a smoothed transition, and FIG. 8B shows the mask from FIG. 7B with a smoothed transition. The region of the B-scan near the edge of each mask will be less attenuated due to the smooth transition from the true image to the background.

Figure 9:
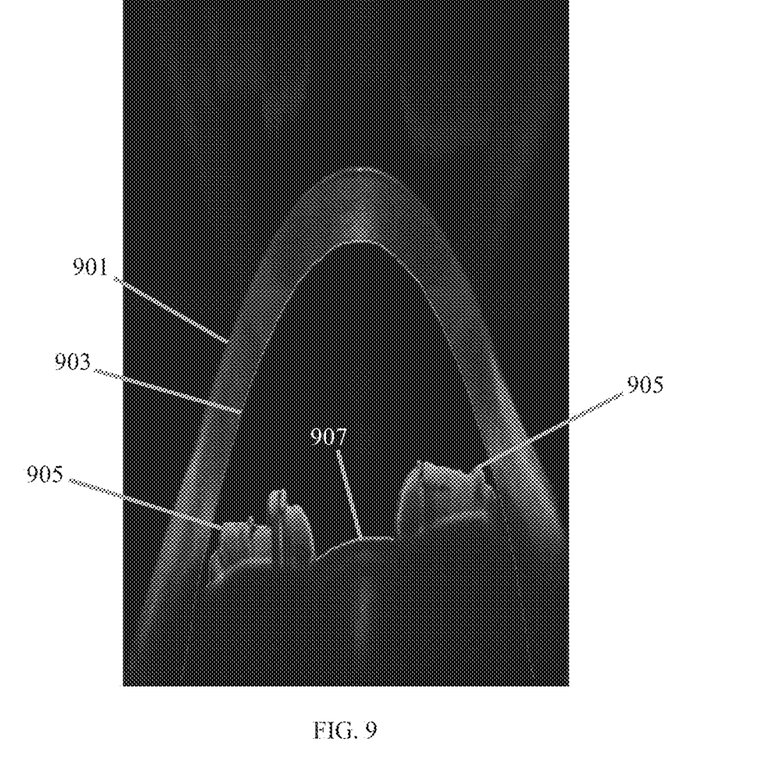
FIG. 9 is a full-range anterior segment B-scan with segmented surfaces and attenuated mirror image.
Figure 10:
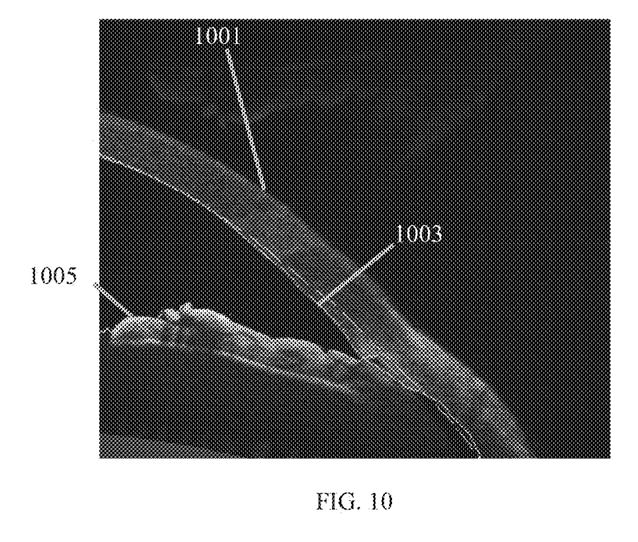
FIG. 10 shows a full-range dewarped irido-corneal angle with segmented surfaces and fits and an attenuated mirror image.

The mirror image and background are then attenuated using these masks. In each B-scan, the pixel values corresponding to portions of either masks having non-zero values are reduced by a percentage. The percentage value is configurable and allows the user to change the attenuation level (from 0% to 100%). FIG. 9 shows an image created using the method described herein with 75% attenuation of the background and mirror image artifact. It also shows the segmentation of the anterior corneal layer 901, posterior corneal layer 903, the iris 905, and the anterior lens capsule 907. In another embodiment, the attenuation can be by greater degree (e.g. 85-95%). FIG. 10 shows a full-range OCT irido-corneal angle scan in which the mirror image artifact has been attenuated. It also shows the results of the automated segmentation of different layers (anterior corneal layer 1001, posterior corneal layer 1003, and iris 1005). The solid lines show the segmented surfaces, and the dashed lines show the quadratic fit of the segmented surfaces.

In addition to using the segmentation information for attenuation, the segmentation information can also be used for certain measurements and for refraction correction and dewarping. For instance, anterior chamber depth and angle can be measured by using the iris and lens segmentation to guide semi- or fully automatic measurements based on user identification of at least one landmark in the image, usually the scleral spur. The posterior and iris segmentations can also be used for semi- or fully automatic angle measurement. Further, refraction correction and dewarping can be performed based on the anterior and posterior surfaces with known refractive indexes. Anterior segment OCT images are distorted by refraction at several boundaries. For instance, rays pass from the air (refractive index of 1.000) into the cornea (refractive index of about 1.372), and from cornea into the aqueous humor (refractive index of about 1.332). The changes in refractive index change the direction of the OCT beam. This type of distortion can be corrected by a dewarping algorithm. Dewarping requires knowledge of the refractive indexes of the cornea and the aqueous humor, as well as the locations of the anterior and posterior corneal surfaces. Thus, dewarping can be performed using the segmentation information determined via the method described above.

Although various applications and embodiments that incorporate the teachings of the present invention have been shown and described in detail herein, those skilled in the art can readily devise other varied embodiments that still incorporate these teachings.

The following references are hereby incorporated by reference:

PATENT REFERENCES

U.S. Pat. No. 8,363,225, "OCT apparatus, methods, and applications" to J. P. Rolland, K. S. Lee, and P. Meemon.

U.S. Pat. No. 7,710,577, "Multiplexing spectrum interference optical coherence tomography" to T. Yatagai and Y Yasuno.

NON-PATENT REFERENCES

A. H. Bachmann, R. A. Leitgeb, and T. Lasser, "Heterodyne Fourier domain optical coherence tomography for full range probing with high axial resolution," Opt. Express 14: 1487-96 (2006).

J. Canny, "A computational approach to edge detection," IEEE Transactions on Pattern Analysis and Machine Intelligence, PAMI-8(6): 679-98 (1986).

M. A. Choma, C. Yang, and J. A. Izatt, "Instantaneous quadrature low-coherence interferometry with 3×3 fiber-optic couplers," Opt. Lett. 28(22): 2162-64 (2003).

M. A. Choma, M. V. Sarunic, C. Yang, and J. A. Izatt, "Sensitivity advantage of swept source and Fourier domain optical coherence tomography," Opt. Express 11(18): 2183-89 (2003).

A. M. Davis, M. A. Choma, and J. A. Izatt, "Heterodyne swept-source optical coherence tomography for complete complex conjugate ambiguity removal," J. Biomed. Opt. 10(6): 064005 (2005).

J. F. de Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28(21): 2067-69 (2003).

M. A. Fischler and R. C. Bolles, "Random Sample Consensus: A paradigm for model fitting with applications to image analysis and automated cartography," Comm. of the ACM 24(6): 381-95 (1981).

E. Götzinger, M. Pircher, R. A. Leitgeb, and C. K. Hitzenberger, "High speed full range complex spectral domain optical coherence tomography," Opt. Express 13(2): 583-94 (2005).

B. Hofer, B. Považay, B. Hermann, A. Unterhuber, G. Matz, and W. Drexler, "Dispersion encoded full range frequency domain optical coherence tomography," Opt. Express 17(11): 7-24 (2009).

B. Hofer, B. Považay, A. Unterhuber, L. Wang, B. Hermann, S. Rey, G. Matz, and W. Drexler, "Fast dispersion encoded full range optical coherence tomography for retinal imaging at 800 nm and 1060 nm," Opt. Express 18(5): 4898-919 (2010).

R. Leitgeb, W. Drexler, A. Unterhuber, B. Hermann, T. Bajraszewski, T. Le, A. Stingl, and A. Fercher, "Ultrahigh resolution Fourier domain optical coherence tomography," Opt. Express 12(10): 2156-65 (2004).

R. A. Leitgeb, C. K. Hitzenberger, and A. F. Fercher, "Performance of fourier domain vs. time domain optical coherence tomography," Opt. Express 11(8): 889-94 (2003).

R. A. Leitgeb, C. K. Hitzenberger, A. F. Fercher, and T. Bajraszewski, "Phase-shifting algorithm to achieve high-speed long-depth-range probing by frequency-domain optical coherence tomography," Opt. Lett. 28(22): 2201-03 (2003).

R. A. Leitgeb, R. Michaely, T. Lasser, and S. C. Sekhar, "Complex ambiguity-free Fourier domain optical coherence tomography through transverse scanning," Opt. Lett. 32(23): 3453-55 (2007).

M. V. Sarunic, M. A. Choma, C. H. Yang, and J. A. Izatt, "Instantaneous complex conjugate resolved spectral domain and swept-source OCT using 3×3 fiber couplers," Opt. Express 13(3): 957-67 (2005).

S. Timp, "A new 2D segmentation method based on dynamic programming applied to computer aided detection in mammography," Med. Phys. 31(5): 958-71 (2004).

C. Tomasi and R. Manduchi, "Bilateral filtering for gray and color images," Proc. ICCV: 839-46 (1998)

B. J. Vakoc, S. H. Yun, G. J. Tearney, and B. E. Bouma, "Elimination of depth degeneracy in optical frequency domain imaging through polarization-based optical demodulation," Opt. Lett. 31(3): 362-64 (2006).

R. K. Wang, "In vivo full range complex Fourier domain optical coherence tomography," Appl. Phys. Lett. 90(5): 054103 (2007).

V. Westphal, A. M. Rollins, S. Radhakrishnan, and J. A. Izatt, "Correction of geometric and refractive distortions in optical coherence tomography applying Fermat's principle," Opt. Express 10(9): 397-404 (2002).

M. Wojtkowski, A. Kowalczyk, R. Leitgeb, and A. F. Fercher, "Full range complex spectral optical coherence tomography technique in eye imaging," Opt. Lett. 27(16): 1415-17 (2002).

Y. Yasuno, S. Makita, T. Endo, G. Aoki, M. Itoh, and T. Yatagai, "Simultaneous B-M-mode scanning method for real-time full-range Fourier domain optical coherence tomography," Appl. Opt. 45)8): 1861-65 (2006).

S. Yun, G. Tearney, J. de Boer, and B. Bouma, "Removing the depth-degeneracy in optical frequency domain imaging with frequency shifting," Opt. Express 12(20): 4822-28 (2004).

J. Zhang, J. S. Nelson, and Z. P. Chen, "Removal of a mirror image and enhancement of the signal-to-noise ratio in Fourier-domain optical coherence tomography using an electro-optic phase modulator," Opt. Lett. 30(2): 147-49 (2005).

We claim:

1. A method for segmenting full-range images generated by an optical coherence tomography (OCT) system, said system having sample and reference arms and wherein the zero-delay position in the sample is defined as the position at which the optical path lengths of the sample and reference arms are equal, the method comprising:
   acquiring an OCT B-scan of a sample using an interferometer by collecting interfering light between signal light reflected from a sample and reference light, wherein the signal light is scanned transversely across said sample and wherein the sample extends to both sides of the zero-delay position, creating both real and complex conjugate images;
   segmenting at least one tissue surface in said OCT B-scan, wherein the tissue surface extends to both sides of the zero-delay position; and
   storing or displaying the segmented surface.

2. A method as recited in claim 1, wherein the sample is the anterior segment of the eye.

3. A method as recited in claim 2, wherein the tissue surface is one of the anterior or posterior corneal surfaces.

4. A method as recited in claim 2, further comprising segmenting a second tissue surface.

5. A method as recited in claim 4, wherein the knowledge of tissue surfaces is used to separate the real image from the OCT data containing both real and complex conjugate images.

6. A method as recited in claim 5, wherein the complex conjugate image is selectively attenuated.

7. A method as recited in claim 6, wherein the selective attenuation is performed using an adjustable control to vary the degree of attenuation of the complex conjugate image.

8. A method as recited in claim 2, further comprising segmenting the anterior surface of the iris and lens capsule.

9. A method as recited in claim 2, further comprising segmenting the anterior and posterior surfaces of the lens.

10. A method as recited in claim 2, further comprising dewarping the full-range OCT image using the segmented tissue surface.

11. A method as recited in claim 10, further comprising making a measurement from the dewarped OCT image.

12. A method as recited in claim 11, wherein the measurement is one of layer thickness, irido-corneal angle, lens thickness, or anterior chamber depth.

13. A method as recited in claim 11, wherein the measurement is performed automatically.

14. A method for segmenting full-range images generated by an optical coherence tomography (OCT) system, said system having sample and reference arms and wherein the zero-delay position in the sample is defined as the position at which the optical path lengths of the sample and reference arms are equal, the method comprising:
   acquiring OCT B-scan of a sample using an interferometer by collecting interfering light between signal light reflected from a sample and reference light, wherein the signal light is scanned transversely across said sample and wherein the sample extends to both sides of the zero-delay position, creating both real and complex conjugate images;

segmenting at least one tissue surface in said OCT B-scan, wherein the tissue surface extends to both sides of the zero-delay position;

selectively attenuating the complex conjugate image; and storing or displaying the B-scan with the attenuated complex conjugate image.

15. A method as recited in claim 14, wherein the sample is the anterior segment of the eye.

16. A method as recited in claim 15, wherein the tissue surface is one of the anterior or posterior corneal surfaces.

17. A method as recited in claim 15, further comprising segmenting a second tissue surface.

18. A method as recited in claim 17, wherein the knowledge of tissue surfaces is used to separate the real image from the OCT data containing both real and complex conjugate images.

19. A method as recited in claim 14 wherein the hardware of the OCT system is configured to reduce the complex conjugate artifact error and the acquiring, segmenting and selectively attenuating steps are performed to further reduce the complex conjugate artifact error.

20. A method for reducing the central line artifact near the zero-delay position in images generated by an optical coherence tomography (OCT) system, said system having sample and reference arms and wherein the zero-delay position in the sample is defined as the position at which the optical path lengths of the sample and reference arms are equal, the method comprising:

acquiring an OCT B-scan consisting of a series of A-scans using an interferometer by collecting interfering light between signal light reflected from a sample and reference light, wherein the signal light is scanned transversely across said sample;

acquiring a reference frame;

processing the individual A-scans in the B-scan to normalize the fluctuations in sequential A-scan spectra using the reference frame; and storing or displaying the resulting B-scan.

* * * * *